(12) United States Patent
Wang (10) Patent No.: US 9,259,515 B2
(45) Date of Patent: Feb. 16, 2016

(54) IMPLANTABLE MEDICAL DEVICES FABRICATED FROM POLYURETHANES WITH GRAFTED RADIOPAQUE GROUPS

(75) Inventor: Yunbing Wang, Sunnyvale, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 1515 days.

(21) Appl. No.: 12/101,041

(22) Filed: Apr. 10, 2008

(65) Prior Publication Data
US 2009/0259297 A1    Oct. 15, 2009

(51) Int. Cl.
*A61F 2/82* (2013.01)
*A61L 31/14* (2006.01)
*A61L 31/06* (2006.01)
*A61L 31/12* (2006.01)
*A61L 31/18* (2006.01)

(52) U.S. Cl.
CPC ............ *A61L 31/148* (2013.01); *A61L 31/06* (2013.01); *A61L 31/129* (2013.01); *A61L 31/18* (2013.01)

(58) Field of Classification Search
CPC ....................................................... A61F 2/82
USPC ............... 623/1.15, 1.16, 1.34; 424/9.4, 426; 525/437; 977/906; 435/128
See application file for complete search history.

(56) References Cited

U.S. PATENT DOCUMENTS

| | | | |
|---|---|---|---|
| 4,284,506 A | 8/1981 | Tetenbaum et al. | |
| 5,145,935 A | 9/1992 | Hayashi | |
| 5,403,188 A | 4/1995 | Oxman et al. | |
| 5,665,831 A | 9/1997 | Neuenschwander et al. | |
| 6,160,084 A | 12/2000 | Langer et al. | |
| 6,221,997 B1 | 4/2001 | Woodhouse et al. | |
| 6,281,262 B1 | 8/2001 | Shikinami | |
| 6,388,043 B1 | 5/2002 | Langer et al. | |
| 6,475,477 B1 * | 11/2002 | Kohn et al. | 424/78.08 |
| 6,545,384 B1 | 4/2003 | Pelrine et al. | |
| 6,777,524 B1 | 8/2004 | Shimizu et al. | |
| 6,784,273 B1 | 8/2004 | Spaans et al. | |
| 6,841,255 B2 | 1/2005 | Deppisch et al. | |
| 6,991,647 B2 | 1/2006 | Jadhav | |
| 7,074,850 B2 | 7/2006 | Hees et al. | |
| 7,135,128 B2 | 11/2006 | Hippold et al. | |
| 7,419,504 B2 | 9/2008 | Hossainy | |
| 7,935,143 B2 | 5/2011 | Wang | |
| 7,956,100 B2 | 6/2011 | Wang | |
| 7,964,210 B2 | 6/2011 | Wang et al. | |
| 8,043,367 B2 | 10/2011 | Wang | |

(Continued)

FOREIGN PATENT DOCUMENTS

| | | |
|---|---|---|
| EP | 1 382 628 | 1/2004 |
| EP | 1 498 147 | 1/2005 |

(Continued)

OTHER PUBLICATIONS

U.S. Appl. No. 11/729,506, filed Mar. 28, 2007, Wang et al.

(Continued)

*Primary Examiner* — Thomas J Sweet
*Assistant Examiner* — Matthew Schall
(74) *Attorney, Agent, or Firm* — Squire Patton Boggs (US) LLP (57) ABSTRACT

Medical devices, such as stents, fabricated from a polymer including degradable polymer segments joined by di-urethane linkages with radiopaque functional groups chemically bonded to the polymer are disclosed.

14 Claims, 6 Drawing Sheets

(56) References Cited

U.S. PATENT DOCUMENTS

| | | | |
|---|---|---|---|
| 8,147,744 B2 | 4/2012 | Kleiner | |
| 8,172,897 B2 | 5/2012 | Gale et al. | |
| 2001/0044516 A1 | 11/2001 | Kaufhold et al. | |
| 2001/0044651 A1* | 11/2001 | Steinke et al. | 623/1.16 |
| 2002/0103325 A1 | 8/2002 | Bleys et al. | |
| 2003/0130470 A1 | 7/2003 | Bleys et al. | |
| 2004/0014929 A1 | 1/2004 | Lendlein et al. | |
| 2004/0015187 A1 | 1/2004 | Lendlein et al. | |
| 2004/0091982 A1* | 5/2004 | Gee et al. | 435/128 |
| 2004/0106987 A1 | 6/2004 | Palasis et al. | |
| 2004/0110285 A1 | 6/2004 | Lendlein et al. | |
| 2004/0116641 A1 | 6/2004 | Mather et al. | |
| 2004/0127673 A1 | 7/2004 | Sunkara | |
| 2005/0048121 A1 | 3/2005 | East et al. | |
| 2005/0107563 A1 | 5/2005 | Hu et al. | |
| 2005/0112170 A1 | 5/2005 | Hossainy et al. | |
| 2005/0197422 A1 | 9/2005 | Mayadunne et al. | |
| 2005/0238683 A1 | 10/2005 | Adhikari et al. | |
| 2005/0245719 A1 | 11/2005 | Mather et al. | |
| 2005/0283229 A1 | 12/2005 | Dugan et al. | |
| 2006/0041089 A1 | 2/2006 | Mather et al. | |
| 2006/0051394 A1 | 3/2006 | Moore et al. | |
| 2006/0188546 A1 | 8/2006 | Giroux | |
| 2006/0292077 A1* | 12/2006 | Zhao | 424/9.4 |
| 2007/0026043 A1 | 2/2007 | Guan et al. | |
| 2007/0088135 A1 | 4/2007 | Lendlein et al. | |
| 2007/0155906 A1 | 7/2007 | Hissink et al. | |
| 2007/0225387 A1 | 9/2007 | Mayadunne et al. | |
| 2007/0270566 A1 | 11/2007 | Lee et al. | |
| 2007/0282426 A1 | 12/2007 | Wang et al. | |
| 2007/0282435 A1 | 12/2007 | Wang et al. | |
| 2008/0033540 A1 | 2/2008 | Wang et al. | |
| 2008/0058919 A1 | 3/2008 | Kramer-Brown | |
| 2008/0147175 A1 | 6/2008 | Krivoruchko et al. | |
| 2008/0208167 A1 | 8/2008 | Stankus et al. | |
| 2008/0249608 A1* | 10/2008 | Dave | 623/1.16 |
| 2008/0262613 A1 | 10/2008 | Gogolewski | |
| 2008/0268019 A1 | 10/2008 | Badylak et al. | |
| 2008/0312315 A1 | 12/2008 | Daniloff et al. | |
| 2008/0319132 A1 | 12/2008 | Lendlein et al. | |
| 2009/0004243 A1 | 1/2009 | Pacetti et al. | |
| 2009/0035350 A1 | 2/2009 | Stankus et al. | |
| 2009/0041845 A1 | 2/2009 | Kleiner et al. | |
| 2009/0081270 A9 | 3/2009 | Moore et al. | |
| 2009/0099600 A1 | 4/2009 | Moore et al. | |
| 2009/0110713 A1 | 4/2009 | Lim et al. | |
| 2009/0163664 A1 | 6/2009 | Lendlein et al. | |
| 2009/0175921 A1 | 7/2009 | Gunatillake et al. | |
| 2009/0181063 A1 | 7/2009 | Ngo et al. | |
| 2009/0182415 A1 | 7/2009 | Wang | |
| 2009/0324675 A1 | 12/2009 | Gunatillake et al. | |
| 2009/0326642 A1 | 12/2009 | Wang | |
| 2012/0038087 A1 | 2/2012 | Wang | |
| 2012/0149850 A1 | 6/2012 | Kleiner | |
| 2012/0150283 A1 | 6/2012 | Kleiner | |

FOREIGN PATENT DOCUMENTS

| | | |
|---|---|---|
| EP | 1 891 993 | 2/2008 |
| EP | 1 932 551 | 6/2008 |
| WO | WO 99/60920 | 12/1999 |
| WO | WO 2007/084444 | 7/2007 |
| WO | WO 2007/139931 | 12/2007 |
| WO | WO 2008/119973 | 10/2008 |
| WO | WO 2008/121508 | 10/2008 |
| WO | WO 2009/058694 | 5/2009 |
| WO | WO 2009/129503 | 10/2009 |
| WO | WO 2009/148926 | 12/2009 |
| WO | WO 2010/021883 | 2/2010 |

OTHER PUBLICATIONS

U.S. Appl. No. 11/784,925, filed Apr. 9, 2007, Wang et al.
U.S. Appl. No. 11/810,464, filed Jun. 5, 2007, Wang et al.
U.S. Appl. No. 11/810,627, filed Jun. 5, 2007, Wang et al.
U.S. Appl. No. 11/864,729, filed Sep. 28, 2007, Wang.
Meredith et al., "LCST phase separation in biodegradable polymer blends: poly(D,L-lactide) and poly($\epsilon$-caprolactone)", Macromol. Chem. Phys. 201, No. 6, pp. 733-739 (2000).
Miller et al., "Degradation Rates of Oral Resorbable Implants (Polylactates and Polyglycolates): Rate Modification with Changes in PLA/GPA Copolymer Ratios", J. Biomed. Mater. Res. vol. 11, pp. 711-719 (1977).
Wang et al., "Polyethylene-Poly(L-lactide) Diblock Copolymers: Synthesis and Compatibilization of Poly(L-lactide)/Polyethylene Blends", J. of Polymer Science vol. 39, pp. 2755-2766 (2001).
International Search Report for PCT/US2009/038978, mailed Jul. 6, 2010, 5 pgs.
Jayakrishnan et al., "Synthesis and Polymerization of Some Iodine-containing Monomers for Biomedical Appllications", J. of Applied Pol. Science, vol. 44, pp. 743-748 (1992).
Kruft et al., "Studies on radio-apaque polymeric biomaterials with potential applications to endovascular prostheses", Biomat. vol. 17, No. 18, pp. 1803-1811 (1996).
International Search Report for PCT/US2009/048040, mailed Sep. 17, 2010, 14 pgs.
James et al., "Polyurethanes with radiopague properties", Biomaterials 27, pp. 160-166 (2006).
International Search Report for PCT/US2009/041031, mailed Jul. 30, 2010, 4 pgs.
International Search Report for PCT/US2009/053476, mailed Aug. 6, 2010, 4 pgs.
International Search Report for PCT/US2009/054533, mailed Aug. 3, 2010, 4 pgs.
Chen et al., "Preparation and Characterization of biodegradable PLA polymeric blends", Biomaterials 24 pp. 1167-1173 (2003).
Jeong et al., "Drug release from biodegradable injectable thermosensitive hydrogel of PEG-PLGA-PEG triblock copolymers", J. of Controlled Release vol. 63, pp. 155-163 (2000).
Lendlein et al."Shape-Memory Polymers", Angew. Chem. Int. Ed. 41, pp. 2034-2057 (2002).
Polyethylene Glycol 1000 MSDS, Material Safety Data Sheet, Science Lab. Com (accessed 2011), 5 pgs.
Middleton et al., "Synthetic Biodegradable Polymers as Medical Devices", Published Mar. 1998, downloaded from: www.mddionline.com/print/3282, Jun. 17, 2013.
Gross et al., "Biodegradable Polymers for the Environment", Science vol. 297, pp. 803-807 (2002).

* cited by examiner

IMPLANTABLE MEDICAL DEVICES FABRICATED FROM POLYURETHANES WITH GRAFTED RADIOPAQUE GROUPS

BACKGROUND OF THE INVENTION

1. Field of the Invention

This invention relates to implantable medical devices fabricated from biodegradable polymers and methods of fabricating such implantable medical devices. In particular, the invention relates to polymers with radiopaque groups grafted to the polymer.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent, "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. The stent may be visualized during delivery and deployment using X-Ray fluoroscopy if it contains radiopaque materials.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with polymeric stents include inadequate toughness and a degradation rate that is slower than is desirable for certain treatments. Another problem with polymeric stents is that polymers tend to be radiolucent, and thus cannot be visualized with X-ray fluoroscopy.

SUMMARY OF THE INVENTION

Various embodiments of the present invention include a stent comprising a stent body fabricated from a polymer including degradable polymer segments joined by di-urethane linkages, and wherein radiopaque functional groups are chemically bonded to the polymer.

Additional embodiments of the present invention include a stent comprising a stent body formed from a biodegradable polymer, wherein radiopaque functional groups are chemically bonded to the polymer.

Further embodiments of the present invention include a method of fabricating a stent comprising: reacting at least one type of biodegradable polymer diol and a di-isocyanate to form a polyurethane comprising biodegradable polymer segments joined by di-urethane linkages; grafting radiopaque functional groups to the backbone of the biodegradable polyurethane to form a radiopaque polymer; and forming a stent body comprising the radiopaque polymer.

DETAILED DESCRIPTION OF THE INVENTION

As used herein, an "implantable medical device" includes, but is not limited to, self expandable stents, balloon-expandable stents, stent-grafts, and generally tubular medical devices.

An implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figure 1:
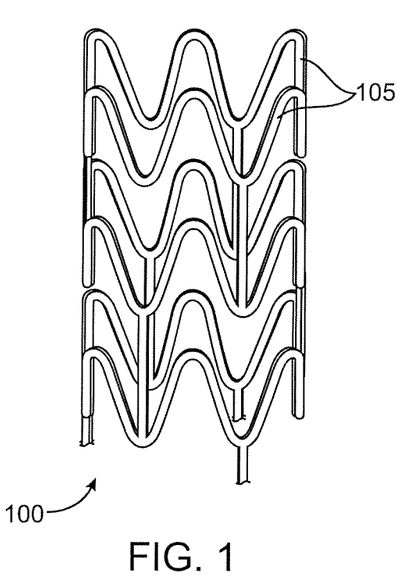
FIG. 1 depicts a stent.

FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Polymers generally do not possess sufficient radiographic density to be easily imaged by fluoroscopy. Since a device such as a stent also has specific mechanical requirements, it is important that rendering a polymeric stent sufficiently radiopaque for imaging does not significantly impact its mechanical behavior. One way to improve the imaging of polymeric materials is to incorporate radiopaque filler materials into a polymeric material to enhance radiographic density. However, such materials may adversely affect the mechanical properties of the polymer, such as strength and toughness.

An alternative to filler materials is to fabricate a stent from polymers having radiopaque dye or functional group covalently bonded to the polymer backbone and end groups. It is believed that the radiopaque density of the stent can be enhanced by the radiopaque functional groups without significantly impacting mechanical properties of the stent. Embodiments of the present invention include a stent formed from a biodegradable polymer in which radiopaque functional groups are chemically bonded to the biodegradable polymer.

A radiopaque functional group can be any chemical group or species that can be bonded to a polymer backbone that increases or enhances the radiographic density of the polymer. Representative examples of radiopaque compounds from which radiopaque groups are derived include iodine, triiodobenzoyl chloride and triiodobenzoic acid.

Additionally, some polymers that may be suitable for implantable medical devices such as stents have potential shortcomings. For example, some crystalline or semi-crystalline polymers may be selected primarily on the basis of strength and stiffness at physiological conditions so that the stent substrate or scaffolding can provide adequate support for a lumen. Physiological conditions refer to conditions within a human patient including, but not limited to, body temperature. Such polymers may be glassy or have a Tg above body temperature making them stiff and strong at body temperature which is approximately 37° C. A "glassy polymer" refers to a polymer having Tg above body temperature. One such shortcoming of such crystalline or semi-crystalline polymers is that their toughness is lower than desired, in particular, for use in stent applications. For example, polymers such as poly(L-lactide) (PLLA), polyglycolide (PGA), or copolymers thereof, poly(L-Lactide-co-glycolide) (PLGA), tend to be brittle under physiological conditions or conditions within a human body.

PGA, which is the simplest linear aliphatic polyester, degrades by hydrolysis of the easily accessible and hydrolytically unstable aliphatic-ester linkages. The degradation time, usually a few months, depends on multiple factors like molecular weight, degree of crystallinity, crystal morphology, and physico-chemical characteristics of the environment.

While structurally very similar to PGA, PLLA has some quite different chemical, mechanical and physical properties due to the presence of a pendant methyl group on the alpha carbon. This makes the PLLA a chiral molecule and the D, L, and DL isomers are possible. PLLA are semicrystalline polymers, while D,L-PLA is a completely amorphous material. The methyl group in PLLA makes the carbonyl of the ester link sterically less accessible to hydrolytic attack, which, depending on certain factors like the type of PLLA, its molecular weight, and its degree of crystallinity, makes the PLLA typically more hydrolytically stable than PGA when exposed to the same environment.

Another shortcoming of some biodegradable polymers is their degradation rate can be slower or faster than desired for certain stent treatments. For instance, the degradation rate may be too slow. As a result, the degradation time of a stent made from such a polymer can be longer than desired. Reducing degradation time allows further surgery or intervention, if necessary, on a treated vessel to occur sooner. Additionally decreasing degradation time helps cut down on the cases of late stent thrombosis, a condition in which clots form on the surface of the stent months or years after deployment. For example, a stent made from PLLA can have a degradation time of between about two and three years or longer. "Degradation time" refers to the time for a stent implanted in a vessel to completely absorb. "Degradation time" can also refer to the time for a stent to completely absorb under in vitro conditions. In some treatment situations, a degradation time of less than a year may be desirable, for example, between six and 12 months, or more narrowly, between eight and ten months.

The degradation of a hydrolytically degradable polymer follows a sequence including water penetration into the polymer followed by hydrolysis of bonds in the polymer. Thus, the degradation of a polymer can be influenced by its affinity for water and the diffusion rate of water through the polymer. A hydrophobic polymer has a low affinity for water which results in a relatively low water penetration. In addition, the diffusion rate of water through crystalline regions of a polymer is lower than amorphous regions. Thus, as either the affinity of a polymer for water decreases or the crystallinity increases, water penetration and water content of a polymer decreases, resulting in a slower degradation rate.

Various embodiments of the present invention include an implantable medical device, such as a stent, formed from a biodegradable polymer having radiopaque functional groups chemically bonded to the polymer. The radiopaque groups allow the stent to be visualized upon implantation within a body of a patient. In such embodiments, the radiopaque functional groups can be chemically bonded to or along the backbone of the polymer. Additionally, the radiopaque functional groups can also be bonded to end groups of the polymer.

In certain embodiments, an implantable medical device can be fabricated from a polymer including degradable polymer segments joined by di-urethane linkages. In such embodiments, the radiopaque functional groups may be chemically bonded to the di-urethane linkages along the backbone of the polymer. In some embodiments, the polymer can have the same type of polymer segments joined by the di-urethane linkages throughout the polymer chain. In an alternative embodiment, the polymer can have different types of polymer segments. In each of these embodiments, the polymer segments can be homopolymers or copolymers.

In all such embodiments, one or more structural elements or struts of a stent can be fabricated from the polymer. In other such embodiments, the body, backbone, scaffolding, or substrate of a stent can be made from the polymer. The body, scaffolding, or substrate may be primarily responsible for providing mechanical support to walls of a bodily lumen once the stent is deployed within the bodily lumen. A stent body, backbone, scaffolding, or substrate can refer to a stent structure with an outer surface to which no coating or layer of material different from that of which the structure is manufactured. If the body is manufactured by a coating process, the stent body can refer to a state prior to application of additional coating layers of different material. By "outer surface" is meant any surface however spatially oriented that is in contact with bodily tissue or fluids. A stent body, backbone, scaffolding, or substrate can refer to a stent structure formed by laser cutting a pattern into a tube or a sheet that has been rolled into a cylindrical shape.

In some embodiments, a majority, substantially all, or all of the stent body, scaffolding, or substrate can be made from the polymer. Substantially all of the body can refer to greater than 90%, 95%, or greater than 99% of the body.

As described in more detail below, embodiments of the radiopaque polymer of the present invention can be made from a polyurethane polymer that includes biodegradable polymer segments joined by di-urethane linkages. The general form of such a polyurethane polymer is:

HO—(P$_1$—O(CO)NH—R—NH(CO)O—P$_2$)$_n$—OH where P$_1$ is a first type of polymer segment, P$_2$ is a second type of polymer segment, NH(CO)O and O(CO)NH are urethane groups, and O(CO)NH—R—NH(CO)O is the di-urethane linkage. R is a functional group derived from a di-isocyanate, which is one of the reactants used in the formation of the polyurethane polymer. P1 or P2 have the form: -M$_n$-R$_1$-M$_n$-, wherein M$_n$ is a polymer or oligomer segment of monomer units. R$_1$ is a functional group derived from an alcohol used in the synthesis of the polymer or oligomer segment. The polymer or oligomer segments can be virtually any polymer or oligomer segment that can be incorporated into the synthesis scheme described below or a synthesis scheme known to one of ordinary skill in the art of polymer chemistry to synthesize the polyurethane polymer stricture provided above. Exemplary polymer or oligomer segments include PLLA, PGA, PLGA, polycaprolactone (PCL) and poly(trimethylene carbonate) (PTMC), polydioxanone (PDO), poly(4-hydroxy butyrate) (PHB), and poly(butylene succinate) (PBS).

As described in more detail below, the polyurethane polymer can be formed by reacting at least one type of polyol with a di-isocyanate (O=C=N—R—N=C=O). Various kinds of di-isocyanates can be used, such as aliphatic and aromatic di-isocyanates. Exemplary di-isocyanates include, but are not limited to, di-isocyanatomethane, di-isocyanatobutane, di-isocyanatoethane, di-isocyanatohexane, di-isocyanatocubane, lysine di-isocyanate, and di-isocyanatocyclohexane.

As described in more detail below, radiopaque groups can be grafted onto the Backbone of the polyurethane polymer through reaction of a radiopaque compound with —NH groups of the di-urethane linkages in which a radiopaque functional group derived from the radiopaque compound is substituted for protons of the —NH groups. Additionally, a radiopaque functional group can be added to the end of an aliphatic polyester through an esterification reaction. In this reaction, a radiopaque group is substituted for a proton of a hydroxyl end group. The general form of a polyurethane polymer with radiopaque groups (R$_O$) at the ends and along the backbone is as follows:

R$_O$O—(P$_1$—O(CO)NR$_O$R—NR$_O$(CO)O—P$_2$)$_n$—OR$_O$

In some embodiments, the P$_1$ and P$_2$ can be the same and can include semicrystalline polymer or oligomer segments having a Tg above body temperature. Such polymer or oligomer segments are referred to as "hard blocks." Exemplary hard block polymers include PLLA, PGA and Polymandelide (PM). In certain embodiments, all or substantially all of the structural elements of stent can be formed from such a polyurethane polymer. An exemplary radiopaque polyurethane polymer includes R$_O$O—(PLLA-O(CO)NRO—R—NR$_O$(CO)O-PLLA)$_n$-OR$_O$, where PLLA corresponds to -(LLA)$_m$-R$_f$-(LLA)$_m$-.

In further embodiments, the polymer or oligomer segments between di-urethane linkages groups can be a copolymer with functional groups selected to increase the degradation rate of the polymer. Such a functional group can have a greater affinity for water or be more hydrolytically active than other functional groups of the polymer. In a particular embodiment, the matrix copolymer can be poly(L-lactide-co-glycolide) (PLGA). The weight percent of the GA in the copolymer can be at least about 1%, 5%, 10%, 15%, 30%, 40%, 50%, or greater 50%. An exemplary radiopaque polyurethane polymer includes R$_O$O—(PLGA-O(CO)NR$_O$—R—NR$_O$(CO)O—PLGA)$_n$-OR$_O$, where PLGA corresponds to -(GA-co-LLA)$_m$-R$_f$-(GA-co-LLA)$_m$-.

As the literature data in Table 1 shows, the degradation time of PLGA decreases from three to four years to less than six months as the GA content increases from 0 wt % to 50 wt %. PLGA is amorphous throughout a wide range of GA content due to the disruption in the regularity in the polymer chain by the addition of another monomer. The decrease in degradation time is due both to the decreased crystallinity and increased hydrolytic activity of the GA.

TABLE 1

Degradation time of PLGA at different monomer compositions.

| Polymer | Degradation Time (months)[a] |
|---|---|
| PGA | 6-12[1,2] |
| 85/15 PLGA | 5-6[1] |
| 75/25 PLGA | 4-5[1] |
| 65/35 PLGA | 3-4[1] |
| 50/50 PLGA | 1-2[1] |

[1]Medical Plastics and Biomaterials Magazine, March 1998.
[2]Medical Device Manufacturing & Technolog 2005.

Figure 2:
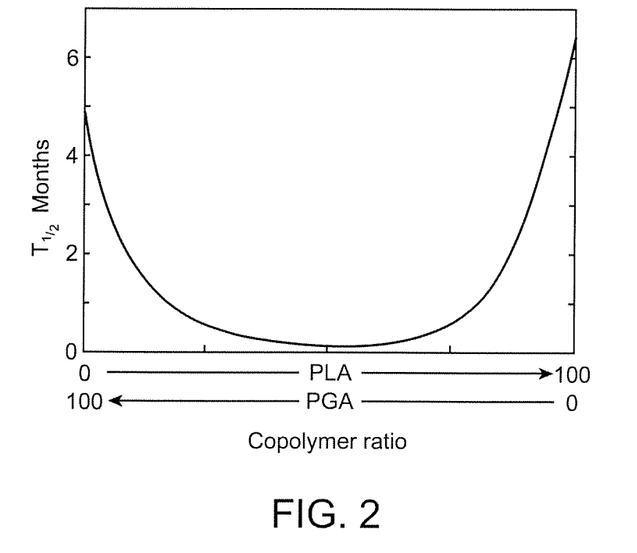
FIG. 2 shows the half-life of PLLA and PGA homopolymers and copolymers implanted in rat tissue.

Furthermore, as shown by FIG. 2, the linear relationship between the copolymer composition and the mechanical and degradation properties of the materials is not linear. FIG. 2 shows the half-life of PLLA and PGA homopolymers and copolymers implanted in rat tissue. Journal of Biomedical Materials Research, 11:711, 1977. The half-life in FIG. 2 refers to the amount of time for the modulus of a polymer to decrease by one half due to degradation of the polymer. For example, a copolymer of 50% GA and 50% LLA degrades faster than either homopolymer.

In some embodiments, a stent scaffolding can be formed from a polyurethane polymer having PLGA segments or oligomers to decrease in degradation time. The decrease can be due to the GA content of the segments or oligomers. In certain exemplary embodiments, the weight percent of GA content can be adjusted so that the degradation time of a stent scaffolding can be less than 24 months, 16 months, 12 months, or more narrowly, less than 12 months.

In additional embodiments, an implantable medical device, such as a stent, can be fabricated at least in part from a radiopaque polyurethane polymer having polymer segments or oligomers with soft blocks. Soft blocks refer to polymers having a Tg below body temperature which tends to be elastomeric at physiological conditions. An "elastomeric" or "rubbery" polymer refers to a polymer which can resist and recover from deformation produced by force, as in natural rubber. In one embodiment, elastomers or rubbery polymers can be stretched repeatedly to at least twice their original length and, immediately upon release of the stress, return with force to their approximate original length. Elastomeric polymers tend to have a percent elongation at break larger than lower toughness polymers, such as brittle polymers. Biodegradable soft block polymers include, but are not limited to, polycaprolactone (PCL) and poly(trimethylene carbonate) (PTMC), polydioxanone (PDO), poly(4-hydroxy butyrate) (PHB), and poly(butylene succinate) (PBS). An exemplary radiopaque polyurethane polymer having soft block polymer segments includes $R_O$O—(PDO-O(CO)NR$_O$—R—NR$_O$(CO)O-PDO)$_n$—OR$_O$, where PDO corresponds to -(DO)$_m$—R1-(DO)$_m$—.

In further embodiments, an implantable medical device can be fabricated at least in part radiopaque polyurethane polymer having hard block and soft block polymer segments. The soft block segments can increase the toughness of the polyurethane polymer. Additionally, a soft block polymer segment with a higher degradation rate than the hard block polymer segment can decrease the degradation time of a device. An exemplary radiopaque polyurethane polymer with hard had soft blocks can include: $R_O$O—(PLLA-O(CO)NR$_O$—R—NR$_O$(CO)O-PDO)$_n$—OR$_O$. The toughness and degradation rate can be tuned by the weight percent of the soft blocks in the polymer. In some embodiments, the molecular weight of the soft blocks can be between about 0.2 kg/mol to 2 kg/mol, 2 kg/mol to 20 kg/mol, or greater than 20 kg/mol.

In other embodiments, the soft block segment can be a copolymer. Exemplary copolymer soft blocks can be P(GA-co-CL), (GA-co-TMC), P(DO-co-CL) or P(DO-co-TMC). random or alternating copolymer segments. An exemplary block copolymer can include HO—(PLLA-O(CO)NH—R—NH(CO)O—P(GA-co-CL))$_n$—OH.

In some embodiments, a device body can be composed of all or substantially all of the polyurethane polymer. Substantially all can refer to more than 95 wt %.

Embodiments of the radiopaque polyurethane polymers described herein can be formed by solution-based polymerization. In other embodiments, such polymers can be formed through melt phase polymerization. In solution-based polymerization, in each of the synthesis steps the reactive components involved in the polymerization reaction are dissolved in a solvent. In melt phase polymerization, the reactions can take place, for example, in a mixing device such as extruder.

A radiopaque polyurethane polymer can be formed in three steps. In the first step, biodegradable polymer chains with —OH or —NH$_2$ end groups are prepared through polymerization of monomer units. The chain length can be controlled by changing the ratio of monomer units to initiator, the reaction time and reaction temperature. In the second step, the polymer chains are connected together through the reaction between their end groups and di-isocyanate. The di-isocyanate functional groups in the polymer that is formed has reactive —NH groups. In the third step, radiopaque groups are grafted onto the backbone of the polymer through reaction of iodine-substituted compounds with —NH groups.

Figure 3:
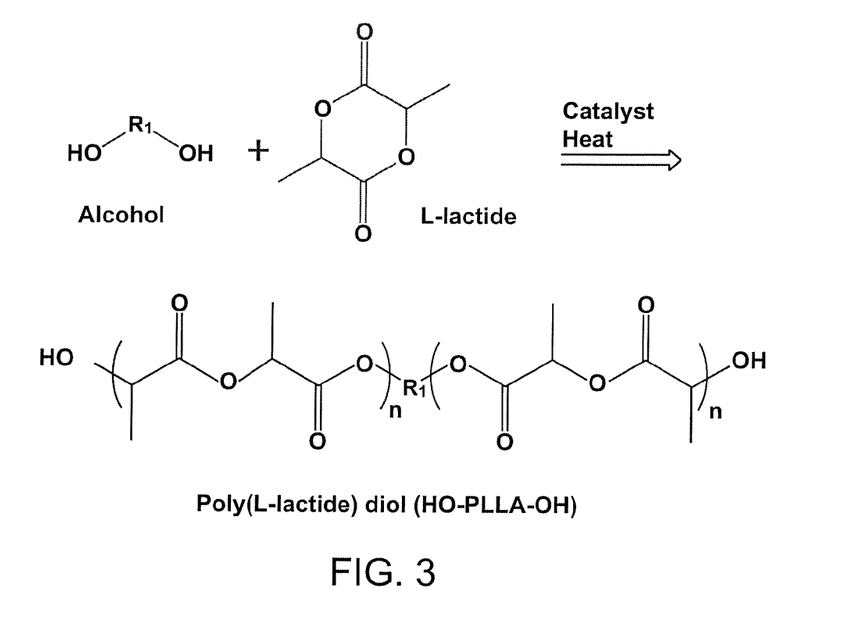
FIG. 3 depicts synthesis of PLLA diol.

As an illustration, a first step involving the formation of a PLLA diol is as follows:

HO—R$_I$—OH+LLA→HO-(LLA)$_n$-R$_I$-(LLA)$_n$-OH    (I)

where HO— R$_I$—OH is a diol initiator with a functional group R$_I$, HO-(LLA)$_n$-R$_I$-(LLA)$_n$-OH is a PLLA diol which will be written as HO-PLLA-OH. An exemplary diol initiator is ethylene glycol. The reaction occurs at an elevated temperature (normally greater than 80° C.) in a suitable solvent and in the presence of a suitable catalyst such a stannous octoate. The reaction is further illustrated in FIG. 3.

Figure 4:
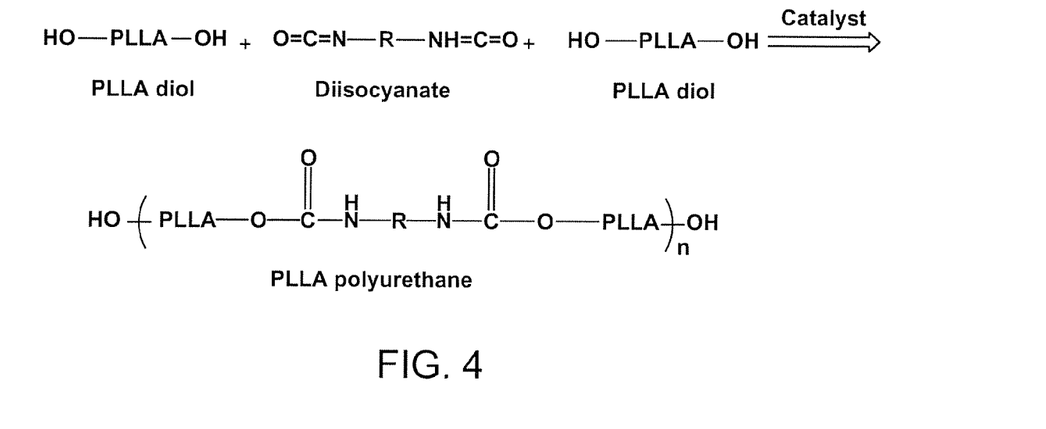
FIG. 4 depicts the synthesis of a polyurethane polymer with PLLA segments.

The PLLA diols react in solution with a di-isocyanate in the presence of a catalyst to form a polyurethane polymer as follows:

HO-PLLA-OH+HO-PLLA-OH+O=C=N—R—
N=C=O→HO-(PLLA-O(CO)NH—R—
NH(CO)O-PLLA)$_n$-OH    (II)

The reaction is further illustrated in FIG. 4. The reaction occurs at room temperature (20-30° C.) or at an elevated temperature (greater than room temperature) in a suitable solvent and in the presence of a suitable catalyst such as stannous octoate.

Figure 5:
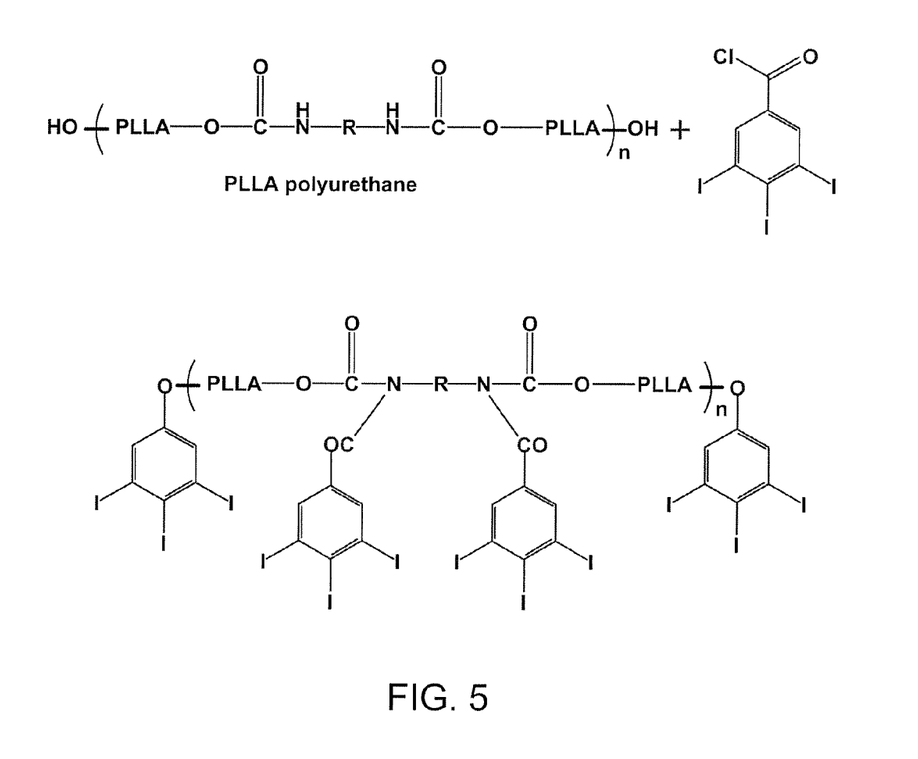
FIG. 5 depicts synthesis of radiopaque polyurethane polymer from the polymer shown synthesized in FIG. 4 and triiodobenzoyl chloride.

Iodine-substituted compounds such as triiodobenzoyl chloride, triiodobenzoyl bromide or triiodobenzoic acid can then be added to a solution containing synthesized PLLA diol polymer. The triiodobenzoyl chloride reacts with the PLLA diol polymer as follows:

HO-(PLLA-O(CO)NH—R—NH(CO)O-PLLA)$_n$-OH+
C$_6$H$_2$I$_3$COCL→R$_O$O-(PLLA-O(CO)NR$_O$—R—
NR$_O$(CO)O-PLLA)$_n$-OR$_O$    (III)

where R$_O$ is C$_6$H$_2$I$_3$CO—.

The triiodobenzoyl group is substituted for the protons of the end groups and the —NH groups. The reaction is further illustrated in FIG. 5.

Iodine-substituted compounds such as triiodobenzoyl chloride or triiodobenzoic acid can then be added to a solution containing synthesized polyurethane block copolymer. Following synthesis of the radiopaque polyurethane polymer, the polymer is precipitated from the reaction solution by pouring the solution into a nonsolvent of the polymer.

Figure 6:
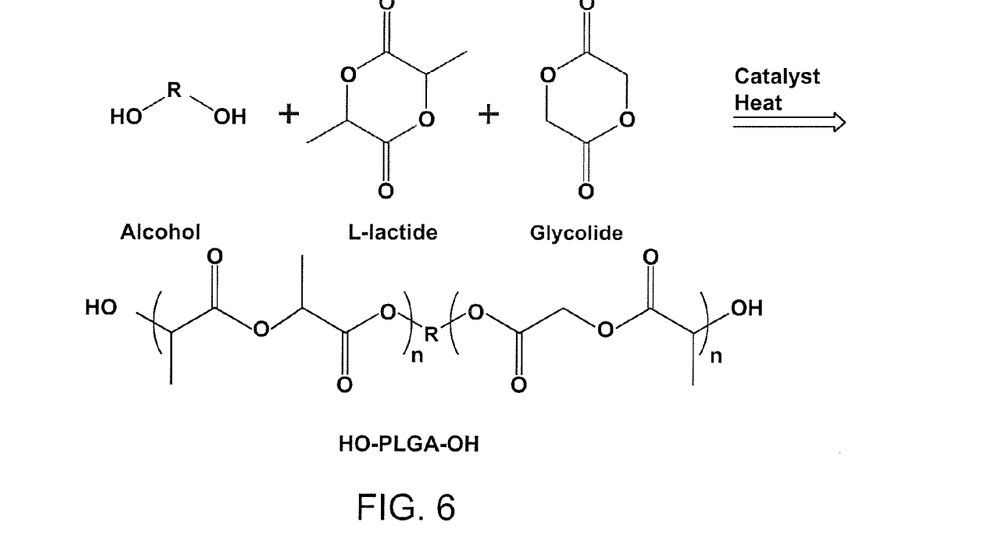
FIG. 6 depicts synthesis of PLGA diol.

As a further illustration, a first step involving the formation of a PLGA diol is as follows:

$$HO-R_f-OH+GA+LLA \rightarrow HO\text{-}(GA\text{-}co\text{-}LLA)_n\text{-}R_f\text{-}(GA\text{-}co\text{-}LLA)_n\text{-}OH \quad (IV)$$

where HO-(GA-co-LLA)$_n$-R$_f$-(GA-co-LLA)$_n$-OH is a PLGA diol which will be written as HO-PLGA-OH. The reaction occurs in at an elevated temperature (normally greater than 80° C.) in a suitable solvent and in the presence of a suitable catalyst such a stannous octoate. The reaction is further illustrated in FIG. 6.

Figure 7:
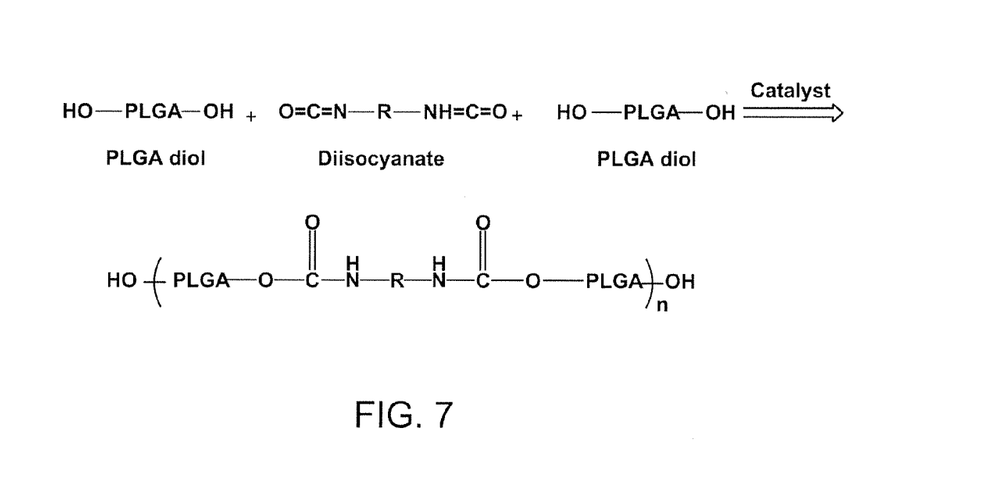
FIG. 7 depicts the synthesis of a polyurethane polymer with PLGA segments.

The PLGA diol reacts in solution with a di-isocyanate in the presence of a catalyst to form a polyurethane polymer as follows:

$$HO\text{-}PLGA\text{-}OH+HO\text{-}PLGA\text{-}OH+O=C=N-R-N=C=O \rightarrow HO-(PLGA\text{-}O(CO)NH-R-NH(CO)O\text{-}PLGA)_n\text{-}OH \quad (V)$$

The reaction is further illustrated in FIG. 7. The reaction occurs at room temperature (20-30° C.) or at an elevated temperature (greater than room temperature) in a suitable solvent and in the presence of a suitable catalyst such a stannous octoate.

Figure 8:
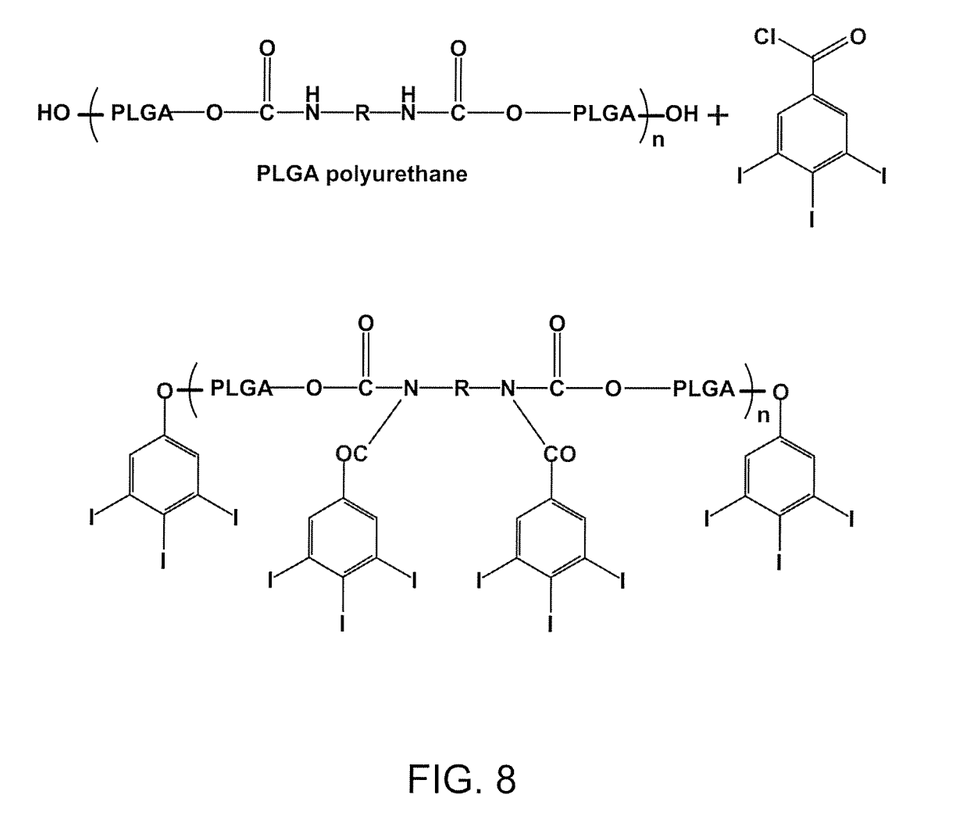
FIG. 8 depicts the synthesis of radiopaque polyurethane polymer from the polymer shown synthesized in FIG. 7 and triiodobenzoyl chloride.

Iodine or an iodine-substituted compound such as triiodobenzoyl chloride can then be added to a solution containing the synthesized polyurethane block copolymer:

$$HO-(PLGA\text{-}O(CO)NH-R-NH(CO)O\text{-}PLGA)_n\text{-}OH+C_6H_2I_3COCL \rightarrow R_OO-(PLGA\text{-}O(CO)NR_O-R-NR_O(CO)O\text{-}PLGA)_n\text{-}OR_O \quad (VI)$$

where $R_O$ is $C_6H_2I_3CO-$.

The triiodobenzoyl group is substituted for the protons of the end groups and the —NH groups. The reaction is further illustrated in FIG. 8. Following synthesis of the radiopaque polyurethane polymer, the polymer is precipitated from the reaction solution by pouring the solution into a nonsolvent of the polymer.

Solvents used in the solution polymerization synthesis of the polymer include, but are not limited to, chloroform, THF, dioxane, toluene, xylene, and cyclohexane. Initiators include, but are not limited to, ethylene glycol, propylene glycol, butanediol and polyethylene glycol. Catalysts used to facilitate the synthesis of the polymer include, but are not limited to, stannous octoate, and stannous trifluoromethane sulfonate.

The intensity of transmitted X-rays, and thus the visibility of a radiopaque material using an imaging technique, depends at least of the weight fraction of radiopaque elements such as iodine in the material. In some embodiments, the fraction of iodine in the radiopaque polymer or stent formed from the polymer can be greater 1-5 wt %, 5-10 wt %, 10-15 wt %, 15-20 wt %, 20-30 wt %, or greater than 30 wt %.

The general form of the radiopaque polymer from above is:

$$R_OO-(P_1-O(CO)NR_O-R-NR_O(CO)O-P_2)_n-OR_O$$

The fraction of iodine in the polymer depends at least on the number of repeat units "n", the molecular weight of P$_1$ and P$_2$, the number of iodine atoms in R$_O$.

The weight fraction of iodine in the polymer is:
MW of all I atoms in polymer/[MW of all I atoms in polymer+MW of all other atoms in polymer]
Specifically, this can be expressed as:

$$2 \times N_I \times MW_I(n+1)/[2 \times N_I \times MW_I(n+1)+2MW_{Rf}(n+1)+2 \times MW_O+n(MW_{P1}+MW_{P2}+MW_{N-R-N})]$$

where N$_I$ is the number of iodine atoms in the radiopaque group, for example, triiodobenzoyl chloride and triiodobenzoic acid each have three iodine atoms per molecule. Rf is functional group bonded to the iodine atom in R$_O$. The molecular properties of the radiopaque polymer can be tailored to obtain a selected or threshold weight fraction, T. From the above relationship, the number of repeat units, n, and the molecular weight of P$_1$ and P$_2$ have the greatest influence on the weight fraction of iodine.

As an illustration, once a value of n is selected, the maximum value of the combined molecular weight of P$_1$ and P$_2$ can be calculated to obtain the threshold weight fraction T. Alternatively, the combined molecular weight of P$_1$ and P$_2$ can be selected to allow calculation of the maximum value of n to obtain the threshold weight fraction T.

In an exemplary embodiment, T=0.15 and n=1, R=—CH$_2$CH$_2$—, R$_O$ is a triiodobenzoyl group. In this example, the combined molecular weight of P$_1$ and P$_2$ must be less than or equal to about 9000 g/mole to provide the desired threshold weight fraction of iodine.

In exemplary embodiments, the molecular weight of P$_1$ or P$_2$ in the polymer can be 200-2000 g/mol, or in some instances greater than 2000 g/mol. In additional exemplary embodiments, the n can be 1-5, 5-10, or greater than 10.

The molecular weight of P$_1$ and P$_2$ can be controlled by the type and amount of diol initiator in, for example, reactions I and IV. The number of repeat units, n, in the polymer can be controlled by the ratio of diol to di-isocyanate in the reaction mixture that forms the polyurethane polymer, for instance, in reactions II and V. It is desirable to have an excess of diol so that the end groups of the formed polymer are hydroxyl groups, however, polymers with di-urethane end groups are within the scope of the present invention. In general, when the diol is in excess, as the ratio of diol to di-isocyanate increases the molecular weight of the formed polymer in reactions II and V tends to decrease. In exemplary embodiments, the ratio of diol to di-isocyanate can be between 1.02 and 1.08. Other embodiments can include ratios outside of this range.

In various embodiments, a stent or stent body or scaffolding can be formed in whole or in part of the radiopaque polymer. In some embodiments, a stent body can be formed of the radiopaque polymer. For example, the body can be formed from a polyurethane radiopaque polymer with PLLA, PLGA, or PLLA or PLGA segments and elastomeric segments. A therapeutic coating can be applied over the body. Embodiments of the radiopaque polymer disclosed herein may be formed into a polymer construct, such as a tube or sheet which can be rolled or bonded to form a tube. An implantable medical device can then be formed from the construct. For example, a stent can be fabricated from a tube by laser machining a pattern in to a tube. In another embodiment, a polymer construct may be formed from the polymer using an injection molding apparatus.

As indicated above, it is important for a stent to have high radial strength so that once it is deployed from the crimped state, it can support a lumen. In general, deforming a polymer construct can strengthen the polymer of the construct along an axis of deformation. In some embodiments of fabricating a stent from a polymer tube, the polymer tube can be radially expanded to increase the radial strength of the tube. The stent can then be fabricated from the polymer tube in its expanded state. Additionally, it has been observed that radially deforming a tube prior to cutting stent patterns increases the toughness of the stent scaffolding. In particular, the radial deformation reduces or eliminates cracks and breaking of the stent struts.

In other embodiments, the radiopaque polymer disclosed herein may be used to form a coating over a device body, such as a stent body. In an embodiment, the polymer segments of P₁ and P₂ may be DL-lactide. The polyurethane PDLA radiopaque polymer may further include a therapeutic agent.

In other embodiments, the stent body can include an abluminal layer and a luminal layer with one of the layers formed from a radiopaque polyurethane. Such a stent body can be formed from a tube having an inner layer and an outer layer, such that one of the layers is composed of a radiopaque polyurethane polymer. Such a tube can be formed through coextrision. A stent body can then be formed by cutting a stent pattern in the coextruded tube.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), poly-orthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxyethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

As indicated above, an implatable medical device such as a stent can be medicated by incorporating an active agent in a coating over the device or within the substrate of the device.

For the purposes of the present invention, the following terms and definitions apply:

"Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

Elongation to Break is the strain on a sample when it breaks. It is usually is expressed as a percent.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples. The Examples below are provided by way of illustration only and not by way of limitation. The parameters and data are not to be construed to limit the scope of the embodiments of the invention.

Example 1

Preparation of Radiopauge PLLA Material

Step 1: Synthesis of PLLA Short Chains with Hydroxyl End Groups (PLLA Diol)
40 g of LLA, 3.1 g ethylene glycol and 80 ml xylene are added into a reactor free of moisture and oxygen. All chemicals are mixed through mechanical stirring and the solution is heated to 90° C. Then 140 mg stannous octoate is added into the reactor and the solution is stirred at 120° C. for 24 h to form PLLA short chains with hydroxyl groups at two ends.
Step 2: Synthesis of PLLA Long Chains with —NH Reactive Functional Groups in the Backbone
Decrease the temperature of the reaction mixture to 90° C., then add 7 g diisocyanatobutane as PLLA chain connector into the reactor and stir the polymerization solution for another 12 hours.
Step 3: Synthesis of Radiopaque PLLA Material
12 hr later, 40 g triiodobenzoyl chloride and 5 ml of triethyl amine are added into the reactor and stirred 10 h to finish the grafting reaction.
The final product is precipitated into 500 ml methanol and dried in a vacuum oven at 80° C. until constant weight.

Example 2

Radiopaque PLGA Material and Stent Preparation

Step 1: Synthesis of PLGA Short Chains with Hydroxyl End Groups (PLGA Diol)
40 g of LLA, 10 g GA, 3.1 g ethylene glycol and 80 ml xylene are added into a reactor free of moisture and oxygen. All chemicals are mixed through mechanical stirring and the solution is heated to 90° C. Then 140 mg stannous octoate is added into the reactor and the solution is stirred at 120° C. for 24 h to form PLGA short chains with hydroxyl groups at two ends.
Step 2: Synthesis of PLGA Long Chains with —NH Reactive Functional Groups in the Backbone
Decrease the temperature of the reaction mixture to 90° C., then add 7 g diisocyanatobutane as PLGA chains connector into the reactor and stir the polymerization solution for another 12 hours.
Step 3: Synthesis of Radiopaque PLGA Material
12 hr later, 40 g triiodobenzoyl chloride and 5 ml of triethyl amine are added into the reactor and stirred 10 h to finish the grafting reaction.
The final product is precipitated into 500 ml methanol and dried in a vacuum oven at 80° C. until constant weight.

Example 3

Stent Preparation from the Radiopaque PLLA or PLGA Material

Step 1: Extrude tubes with designated inside diameter (ID) and outside diameter (OD) (0.02" and 0.07") from the synthesized radiopaque PLLA or PLGA material using a single screw extruder at 200° C.
Step 2: Expand and draw the extruded tubes to improve their mechanical properties along the axial and radial directions.
Step 3: Cut stents from the expanded and drawn tubes using a femto second laser and sterilize all stents after crimping.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A stent comprising a stent body fabricated from a polymer comprising degradable polymer segments joined by di-urethane linkages, wherein radiopaque functional groups are chemically bonded to the di-urethane linkages along the backbone of the polymer.
2. The stent of claim 1, wherein the radiopaque functional groups are derived from a compound selected from the group consisting of triiodobenzoyl chloride, triiodobenzoyl bromide, triidobenzoic acid, and combinations thereof.
3. The stent of claim 1, wherein the di-urethane linkages comprise urethane groups linked by a functional group selected from the group consisting of aliphatic functional groups, aromatic functional groups, and combinations thereof.
4. The stent of claim 1, wherein the polymer segments are selected from the group consisting of poly(L-lactide), polyglycolide, poly(L-Lactide-co-glycolide), and combinations thereof.
5. from the group consisting of polycaprolactone, poly(trimethylene carbonate), poly(4-hydroxy butyrate), polydioxanone, and combinations thereof.
6. A stent comprising a stent body formed from a polymer comprising degradable polymer segments joined by di-urethane linkages;
wherein radiopaque functional groups are chemically bonded to the di-urethane linkages along the backbone of the polymer; and
wherein the degradable polymer segments are selected from the group consisting of poly(L-lactide), polyglycolide, poly(L-Lactide-co-glycolide), polycaprolac- tone, poly(trimethylene carbonate), poly(4-hydroxy butyrate), polydioxanone, and combinations thereof.

7. The stent of claim 6, wherein the radiopaque functional groups are derived from a compound selected from the group consisting of iodine, triiodobenzoyl chloride, triidobenzoic acid, and combinations thereof.

8. A method of fabricating a stent comprising:
reacting at least one type of biodegradable polymer diol and a di-isocyanate to form a polyurethane comprising biodegradable polymer segments joined by di-urethane linkages;
grafting radiopaque functional groups to the di-urethane linkages along the backbone of the polyurethane to form a radiopaque polymer; and
forming a stent body comprising the radiopaque polymer.

9. The method of claim 8, wherein the radiopaque functional groups are grafted onto the di-urethane linkages along the backbone of the polyurethane through reaction of a radiopaque compound with —NH groups of the di-isocyanate linkages.

10. The method of claim 9, wherein the radiopaque compound is selected from the group consisting of iodine, triiodobenzoyl chloride, triidobenzoic acid, and combinations thereof.

11. The method of claim 8, wherein the biodegradable polymer diol is selected from the group consisting of poly(L-lactide) diol, poly(L-Lactide-co-glycolide) diol, and combinations thereof.

12. The method of claim 8, wherein the biodegradable polymer diol is selected from the group consisting of polycaprolactone diol, poly(trimethylene carbonate) diol, poly(4-hydroxy butyrate) diol, polydioxanone diol, and combinations thereof.

13. The method of claim 8, wherein the di-isocyanate comprises an aliphatic di-isocyanate, an aromatic di-isocyanate, or a combination thereof.

14. The method of claim 8, wherein the di-isocyanate is selected from the group consisting of di-isocyanatomethane, di-isocyanatobutane, di-isocyanatoethane, di-i socyanatohexane, di-isocyanatocubane, lysine di-isocyanate, di-isocyanatocycloehexane, and combinations thereof.

* * * * *